(12) United States Patent
Miyazaki et al.

(10) Patent No.: US 7,426,255 B2
(45) Date of Patent: Sep. 16, 2008

(54) X-RAY CT DEVICE

(75) Inventors: Osamu Miyazaki, Ibaraki (JP); Tetsuo Nakazawa, Chiba (JP); Hiroto Kokubun, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 105 days.

(21) Appl. No.: 10/544,907

(22) PCT Filed: Feb. 13, 2004

(86) PCT No.: PCT/JP2004/001531

§ 371 (c)(1),
(2), (4) Date: Aug. 10, 2005

(87) PCT Pub. No.: WO2004/071301

PCT Pub. Date: Aug. 26, 2004

(65) Prior Publication Data

US 2006/0140337 A1   Jun. 29, 2006

(30) Foreign Application Priority Data

Feb. 14, 2003   (JP)   ............................. 2003-036308
Apr. 4, 2003    (JP)   ............................. 2003-101544

(51) Int. Cl.
H05G 1/60   (2006.01)
(52) U.S. Cl. ............................................. 378/8; 378/4
(58) Field of Classification Search .............. 378/4–20,
378/108, 109, 145, 901
See application file for complete search history.

(56) References Cited

U.S. PATENT DOCUMENTS 5,023,895 A * 6/1991 McCroskey et al. ............ 378/4
5,450,462 A * 9/1995 Toth et al. ...................... 378/16
5,751,782 A * 5/1998 Yoshitome ................. 378/98.5
5,832,051 A * 11/1998 Lutz ............................... 378/8
6,094,468 A * 7/2000 Wilting et al. ................. 378/8
6,198,789 B1 * 3/2001 Dafni ............................. 378/8

(Continued)

FOREIGN PATENT DOCUMENTS

DE   19622075 A1   12/1997

(Continued)

*Primary Examiner*—Courtney Thomas
*Assistant Examiner*—Alexander H Taningco
(74) *Attorney, Agent, or Firm*—Cooper & Dunham LLP

(57) ABSTRACT

An X-ray CT apparatus comprises: motion information acquisition means that acquires periodical motion information on a motion portion of an object to be examined; a detector that rotates together with an X-ray source and detects X-rays applied to the object from the X-ray source to acquire projection data per collection region; and reconstruction means that processes the projection data resulting from the detector to reconstruct a tomogram of the object, wherein the X-ray CT apparatus further includes delay time determination means that determines a delay time by adding a time width of the collection region and a processing delay time in the X-ray CT apparatus and a time interval from the moment when the phase of the measured periodical motion information is matched with the phase of the rotation period of the X-ray CT apparatus to the moment when they are matched next time, and collection means that correlates, with the periodical motion information obtained by the motion information acquisition means, and successively collects the projection data obtained from the detector, with the reconstruction means starting reconstruction of the tomogram after the delay time.

19 Claims, 9 Drawing Sheets

U.S. PATENT DOCUMENTS

| | | | |
|---|---|---|---|
| 6,298,111 B1 * | 10/2001 | Ozaki ............................. | 378/8 |
| 6,507,639 B1 * | 1/2003 | Popescu ...................... | 378/108 |
| 6,560,309 B1 * | 5/2003 | Becker et al. ................... | 378/8 |
| 6,836,529 B2 * | 12/2004 | Li et al. .......................... | 378/8 |
| 2006/0133564 A1 * | 6/2006 | Langan et al. .................. | 378/8 |

FOREIGN PATENT DOCUMENTS

| | | |
|---|---|---|
| JP | 7-204189 | 8/1995 |
| JP | 9-75336 | 3/1997 |
| JP | 10-52424 | 2/1998 |
| JP | 2001190547 A * | 7/2001 |
| JP | 2002263097 A * | 9/2002 |
| JP | 2002-325758 | 11/2002 |

* cited by examiner

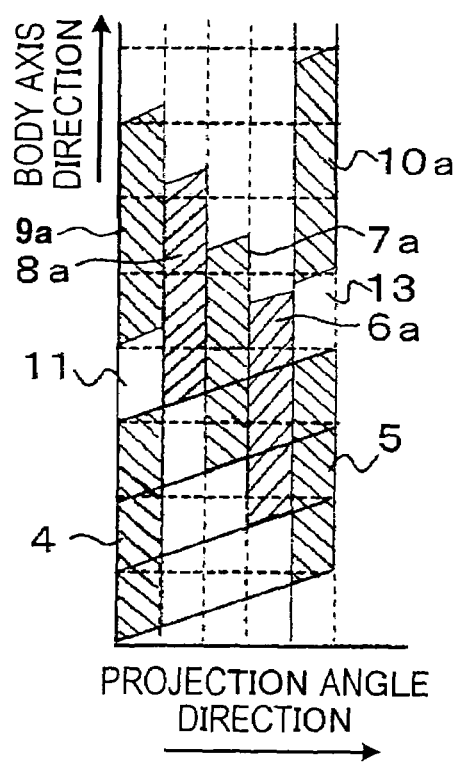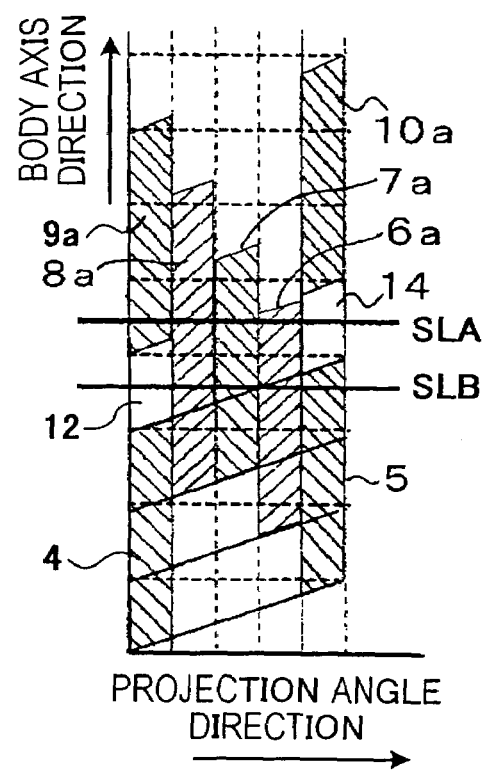

X-RAY CT DEVICE

TECHNICAL FIELD

The present invention relates to technology that enables a reduction in exposure, an improvement in image quality, and an increase in the processing speed of imaging when imaging a moving portion such as a heart, without lowering the diagnostic value of an X-ray CT apparatus.

BACKGROUND ART

It is known that when scanning and reconstruction are not done following the beat of the heart in heart region imaging, a pseudo-image called a motion artifact and blurring occur, which is unsuitable for clinical diagnosis. It is conceivable to hasten as much as possible the scanning speed as one approach to solve this problem, and there is a CT apparatus that uses an electron beam to realize this. This CT apparatus has a scanning speed of about 100 ms and is capable of tomography that is as sharp as if the heart had stopped. However, the cost of this CT apparatus using an electron beam is high, the CT apparatus is large, it is necessary to dispose the CT apparatus in addition to an existing X-ray CT apparatus, and there is the potential for the CT apparatus to become a burden in terms of equipment investment.

Thus, an ECG-gated imaging technique has been proposed which is based on existing X-ray CT apparatuses. This is a technique which successively collects projection data across plural heartbeats on the same slice plane, uses as a reference R waves of electrocardiograph information recorded at the same time, sets the time and heartbeat phase width thereafter, collects only the projection data of the same cardiac time aspect from the data among the plural heartbeats, and reconstructs a tomogram with ECG reconstruction means.

The technique of obtaining an aimed tomogram by extracting the necessary data from among the wealth of projection data when later creating a tomogram in an optional cardiac time aspect in this manner is commonly called retrospective segmented reconstruction. However, retrospective segmented reconstruction has the problem of an increase in patient exposure due to redundant measurement. In order to accommodate this, there is a technique called prospective which systematically acquires projection data necessary for tomogram creation. Because this technique determines in advance the cardiac time aspect to be acquired and applies X-rays aimed only at that range, excess exposure can be avoided.

JP-A-2001-190547 discloses technology that similarly reduces exposure and images moving organs such as the heart with an X-ray CT apparatus. This technology includes a rotating mechanism that rotates/drives an X-ray tube in a state where an object to be examined is sandwiched between the X-ray tube and an X-ray detector, an X-ray control unit that supplies power for applying the X-rays to the X-ray tube, and a reconstruction device into which projection data detected by the X-ray detector are inputted to reconstruct a tomogram. -The object transmittance thickness changes in accordance with the rotation of the X-ray tube and the detector. An increase in noise resulting from needless invalid exposure and insufficient radiation dose occur. If control to reduce the tube current is not done when the object transmittance thickness is short, there is the potential to increase superfluous exposure. Conversely, if control is not done so that the tube current becomes larger when the object transmittance thickness is large, there is the potential to increase image noise. Thus, JP-A-2002-263097 discloses the transmittance thickness-dependent control shown in FIG. 2c. Namely, the tube current is varied in accordance with the rotational angle  and the body axis direction position z from the scanogram. With this technique, the X-rays applied to the object can be greatly reduced because the tube current is controlled in consideration of the transmittance thickness of the object.

Here, it is an object of the present invention to provide an X-ray CT apparatus which, in regard to a periodical motion portion such as a heart, considers both the time aspect during the periodical motion and the X-ray transmittance thickness in the object, pursues reduction of invalid exposure and image quality improvement, is a developed form of prospective scanning and a reconstruction method that also enables retrospective reconstruction, and simultaneously achieves a reduction in the object's exposure to X-rays, an improvement in diagnostic image quality, and an insurance of the freedom of post-imaging reconstruction.

In X-ray CT apparatuses employing the conventional retrospective ECG-gated imaging technique, abnormalities in the motion of the ventricular walls and abnormalities in the coronary artery can be observed because a tomogram of the ventricular wall diastole is taken, but once the heart region has been imaged, the projection data are combined by ECG reconstruction means and image reconstruction processing is conducted. Thus, an image of the heart cannot be observed while imaging the heart region.

Thus, it is another object of the present invention to provide an X-ray CT apparatus that is configured to develop the prospective scanning method and the reconstruction method, reduces the motion artifact stemming from the movement of motion portions such as the heart, and with which an image of the motion portion can be observed in real-time while imaging that motion portion.

DISCLOSURE OF THE INVENTION

According to a first aspect of the invention, an X-ray CT apparatus comprises: motion information acquisition means that acquires periodical motion information on a motion portion of an object to be examined; a detector that rotates together with an X-ray source and detects X-rays applied to the object from the X-ray source to acquire projection data per collection region; and reconstruction means that processes the projection data resulting from the detector to reconstruct a tomogram of the object, wherein the X-ray CT apparatus further includes delay time determination means that determines a delay time by adding a time width of the collection region and a processing delay time in the X-ray CT apparatus and a time interval from the moment when the phase of the measured periodical motion information is matched with the phase of the rotation period of the X-ray CT apparatus to the moment when they are matched next time, and collection means that correlates, with the periodical motion information obtained by the motion information acquisition means, and successively collects the projection data obtained from the detector, with the reconstruction means starting reconstruction of the tomogram after the delay time.

According to a second aspect of the invention, the X-ray CT apparatus further includes reconstruction time aspect specification means that specifies a time aspect in the periodical motion information to be reconstructed, and means that modulates/controls the X-ray source using a motion period-dependent control pattern that controls so that the intensity of the X-rays applied from the X-ray source becomes relatively large in the specified time aspect and a transmittance thickness-dependent control pattern that varies the intensity of the X-rays applied from the X-ray source depending on the X-ray transmittance thickness of the object, and maintains at a constant an output level of the detector, wherein the reconstruction means reconstructs a tomogram of the motion portion from the projection data of the collection region corresponding to the time aspect specified by the reconstruction time aspect specification means.

According to a third aspect of the invention, the X-ray CT apparatus further includes reconstruction time aspect specification means that specifies a time aspect in the periodical motion information to be reconstructed, means that modulates/controls the X-ray source using one of a mode resulting from a motion period-dependent control pattern that controls so that the intensity of the X-rays applied from the X-ray source becomes relatively large in the specified time aspect and a composite mode comprising the motion period-dependent control pattern and a transmittance thickness-dependent control pattern that, varies the intensity of the X-rays applied from the X-ray source depending on the X-ray transmittance thickness of the object, and maintains at a constant an output level of the detector, and selection means that selects and executes one of the mode resulting from the motion period-dependent control pattern and the composite mode, wherein the reconstruction means reconstructs a tomogram of the motion portion from the projection data of the collection region corresponding to the time aspect specified by the reconstruction time aspect specification means.

According to a fourth aspect of the invention, the periodical motion information is the beating of a heart.

According to a fifth aspect of the invention, the reconstruction means reconstructs using the projection data corresponding to collection regions of at least 180 degrees of the rotation.

According to a sixth aspect of the invention, the X-ray CT apparatus further includes interpolation means that interpolates and obtains, from a collection region of other projection data, the collection region of projection data in the slice position to be reconstructed after the elapse of the delay time.

According to a seventh aspect of the invention, the X-ray CT apparatus further includes buffering means that correlates and temporarily retains, with the periodical motion information, the projection data obtained from the collection means and deletes or updates the projection data for which reconstruction has been completed after the delay time.

According to an eighth aspect of the invention, the reconstruction means includes filter means that reduces the noise level difference between the collection regions or between the tomograms.

BRIEF DESCRIPTION OF THE DRAWINGS

FIG. 12 are descriptive diagrams showing another state of a reconstruction method in a conventional X-ray CT apparatus.

BEST MODES FOR IMPLEMENTING THE INVENTION

Embodiments of an X-ray CT apparatus of the present invention will be described below using the drawings.

Embodiment 1

Figure 1:
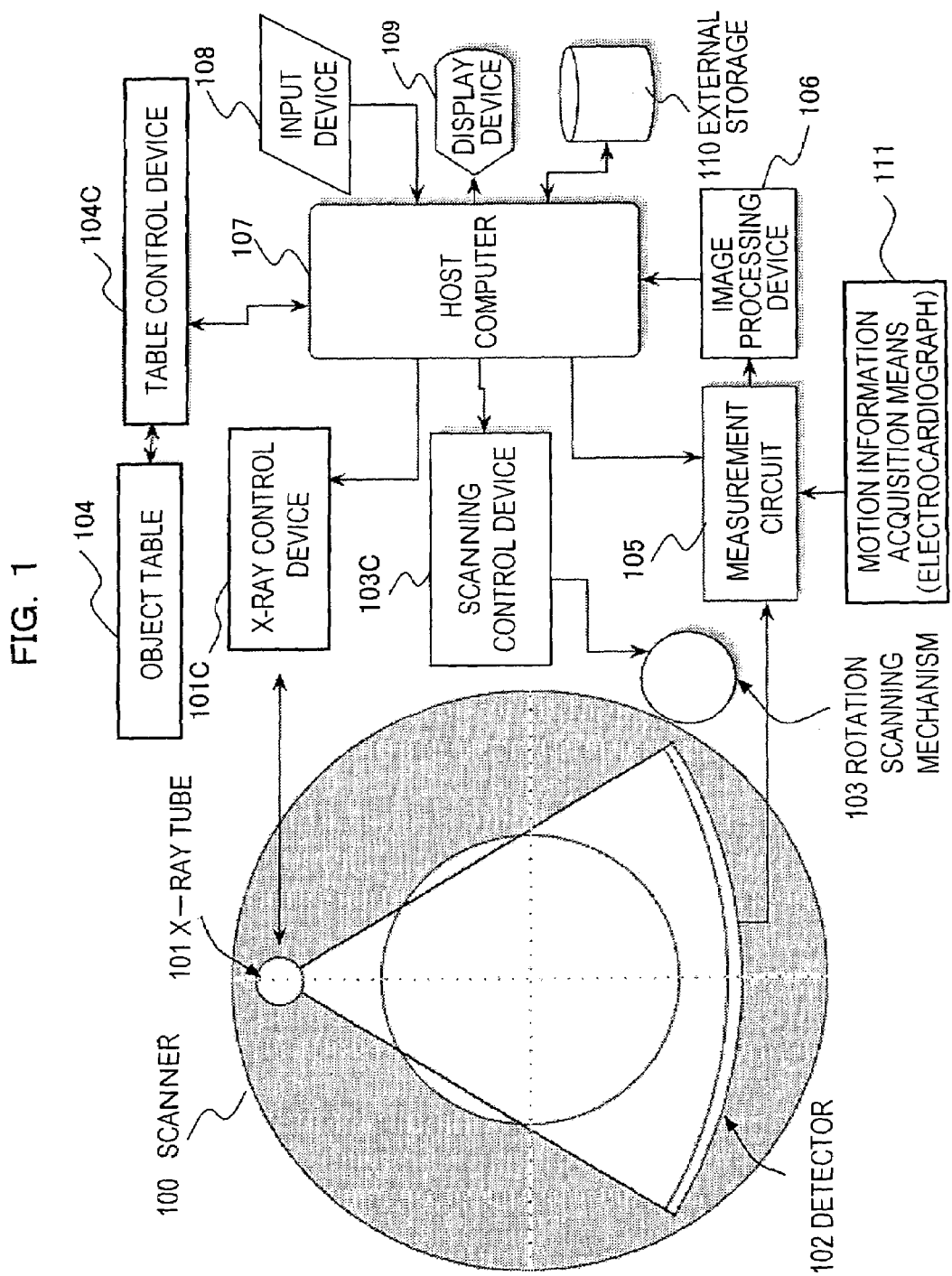
FIG. 1 is a block diagram showing an exemplary configuration of an X-ray CT apparatus according to an embodiment of the present invention.

As shown in FIG. 1, the X-ray CT apparatus includes a host computer 107 that collectively controls the entire system, an X-ray generation system including an X-ray tube 101, a (rotation) scanning mechanism 103 disposed with a detection system including a detector 102, a conveyance-use patient table 104 at the time of patient position determination and helical scanning, an image processing device 106 that implements various kinds of image processing, an external storage device 110, a display device 109, and an input device 108 for an operator to input instruction information. The X-ray CT apparatus is configured so that motion information can be inputted from external motion information acquisition means 111. The motion information is, for example, periodical motion information, and is inputted from the motion information acquisition means 111 to a measurement circuit 105. When projection data per collection region are inputted from the detector 102, the motion information is added to the projection data and sent to the image processing device 106 and the host computer 107. The projection data are data extended in a channel direction of the detector, but because the data are sometimes not valid at the channel end portions, the CT apparatus uses this space to add the motion information. By doing this, the CT apparatus extracts only the data relating to a later-described certain time aspect of the periodical motion.

An X-ray control device 101C that controls the X-ray intensity is disposed on a rotary table of a scanner 100. Prior to the start of imaging, each device is prepared for imaging (setting of imaging conditions, reconstruction conditions). The rotation scanning mechanism 103 rotates the rotary table of the scanner 100, and at the state where a predetermined rotational speed has been reached, the scanning control device 103C notifies the host computer 107 of preparation completion information. In the case of helical scanning, the rotation scanning mechanism 103 moves the rotary table of the scanner 100 in advance to a position in consideration of the acceleration speed of the object table 104 so that the rotational speed becomes a steady speed at the X-ray exposure start position. When the X-ray tube 101 applies the X-rays and starts the imaging, the X-ray tube 101 applies X-rays of an intensity instructed (or for which a tube current control pattern has been preregistered) by the host computer 107 to the opposing detector 102. After the detector 102 detects the X-rays transmitted through the object (not shown) and converts the X-rays to electrical signals, the measurement circuit 105 acquires projection data as digital data. The projection data undergoes image processing in the image processing device 106, beginning with preprocessing, filter processing and reverse projection processing, to reconstruct a tomogram. The reconstructed image is displayed as a diagnostic image by the display device 109.

Next, the flow of the imaging of a motion portion will be described. The X-ray CT apparatus pertaining to the present embodiment includes two control modes: a motion period-dependent control mode and a composite mode comprising motion period-dependent control and transmittance thickness-dependent control.

A case will be described below where the motion portion is a heart, but the motion portion is not limited to the heart and may also include the lungs, the diaphragm, the arteries, the ventriculus, and the intestines.

Prior to heart imaging, the operator selects one of the aforementioned control modes and inputs the selected control mode, the average heartbeat of the object, the target time aspect, and the maximum/minimum tube currents. The host computer 107 calculates the control period of the tube current from the inputted average heartbeat, creates a tube current control pattern 1 that varies between the maximum/minimum tube currents, and transfers the control pattern to the X-ray control device. The motion period-dependent control mode uses the tube current control pattern 1 to start imaging. It has already been mentioned that JP-A-2002-263097 discloses the transmittance thickness-dependent control shown in FIG. 2c. Namely, because the tube current is controlled in consideration of the transmittance thickness of the object in accordance with the rotational angle, and the body axis direction position z from the scanogram, the X-rays applied to the object can be greatly reduced. The present embodiment exceeds this and further reduces invalid exposure to allocate the invalid exposure to the portion necessary for improving image quality. For this reason, according to the present embodiment, the composite mode comprising motion period-dependent control and transmittance thickness-dependent control has been newly invented.

Figure 2:
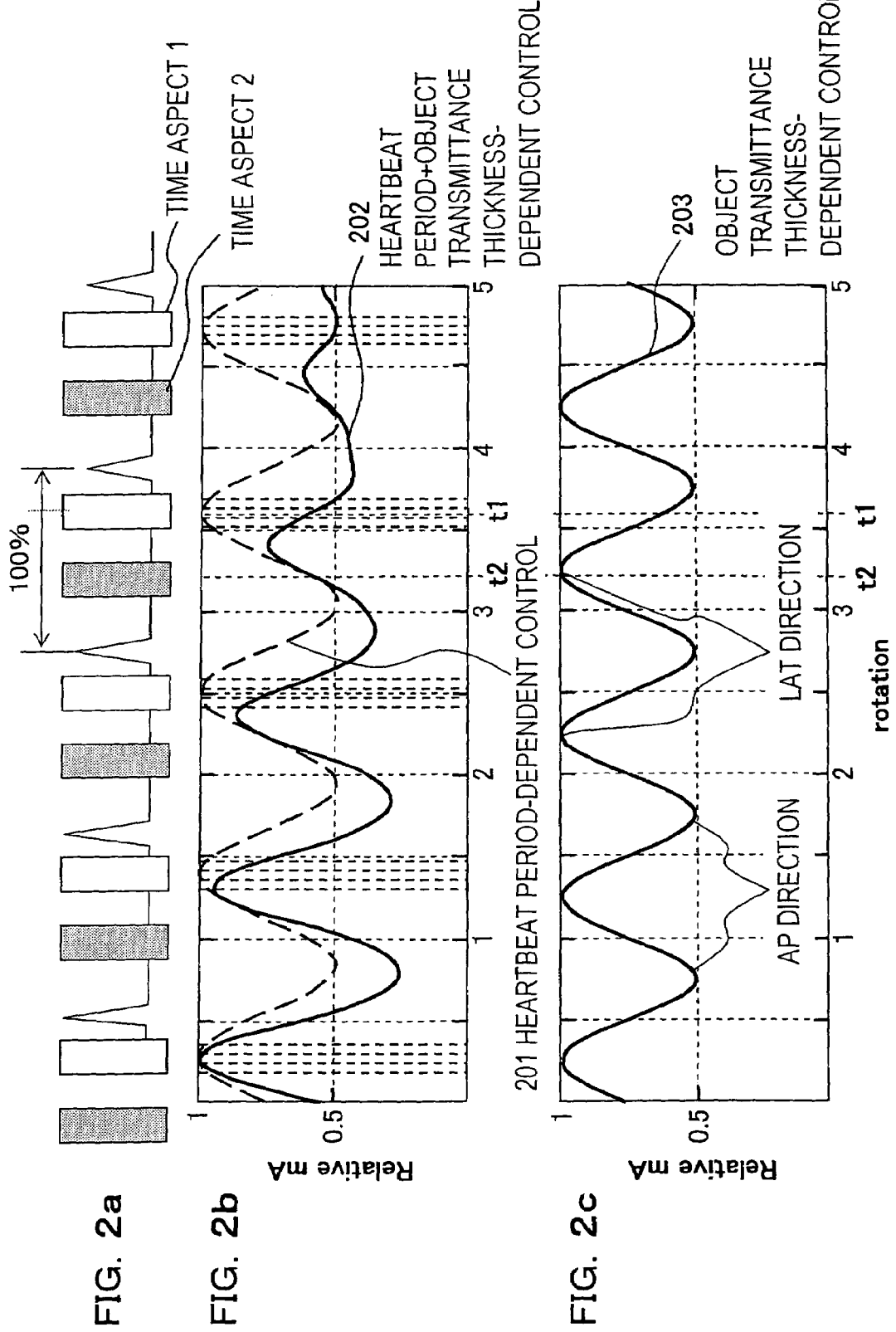
FIG. 2a is a diagram describing an ECG waveform and the positions of a time aspect 1 and a time aspect 2 therein.
FIG. 2b is a diagram describing an example of a tube current control pattern employed in the present invention.
FIG. 2c is a diagram describing an example of an object transmittance thickness tube current control pattern employed in the prior art.

FIG. 2a shows ECG waveform data, and FIG. 2b shows the tube current control pattern according to the present embodiment. FIG. 2c shows a control pattern in a case where the minimum tube voltage is halved in the object transmittance thickness-dependent technique pertaining to the prior art. Below, in order to facilitate description, it will be assumed that there is no change in the cross-sectional shape in the body axis direction. Control waveforms 201 and 203 are controlled to be sine waves as shown in the drawings, but the time width of the target time aspect may be relatively large. In this case, it is preferable to make a pattern in consideration of fluctuations in the heartbeat.

When the tube current is controlled with the heartbeat period-dependent technique of the present embodiment, the control pattern becomes the dotted line 201 of FIG. 2b. Here, similar to the conventional example shown in FIG. 2c, the minimum tube voltage is halved. This case is an example where the target time aspect is a time aspect 1, and is imaging in which the maximum tube current is applied to match the time aspect 1 desired to be seen with the highest image quality of the ECG waveform. It will be understood that because the reconstruction means reconstructs using only the segment data in the target time aspect, the reconstruction means can acquire an excellent image in which there is the least noise. When the case of obtaining an image of another time aspect is considered, e.g., in the time aspect 2 shown in the drawing, the image has a lot of noise because only the data where the tube current is close to the minimum are used. The typical way of determining the target time aspect uses, for example 60to 70% of the time aspect (so-called diastolic phase) as the target time aspect ordinarily, an image of the diastolic phase is used in to calculate the coalification index and evaluate the constriction of the coronary artery, and other time aspects are used to look at the state of motion of the heart wall. Because the motion of the heart wall is often observed with a moving image, the noise usually becomes inconspicuous in comparison to a stationary image and sufficient observation can be done. When analysis is done using a stationary image, high resolution is not needed because an evaluation of blood vessels and the like are not accompanied. Thus, because testing becomes possible with one-time imaging, there is also little exposure.

Turning now to the dotted line 201 in FIG. 2b, in view of transmittance thickness of an object to be examined, it will be understood that, the tube current becomes higher at the time t1 entering the anteroposterior (AP) direction of the object where the transmittance thickness is short and the tube current is desired to be low. It will also be understood that at the time t2, the tube current conversely becomes lower in the lateral (LAT) direction where the tube current is desired to be high. In other words, at the time t1 of the dotted line 201 in FIG. 2b, there is a needless increase in exposure, and at the time t2, the tube current is lowered more than necessary and image noise is increased too much.

The composite mode comprising heartbeat period-dependent control and transmittance thickness-dependent control is a technique that further modulates, with the object transmittance-dependent pattern, the motion period-dependent control pattern. With each being represented by the dotted line 201 in FIG. 2b and the solid line 203 in FIG. 2c, the pattern after modulation becomes the solid line 202 in FIG. 2b. Thus, the image quality can be improved in the target time aspect, and the exposure can be significantly reduced in other time aspects. Noise fluctuation in the rotational angle direction occurring substantially periodically in accompaniment with changes in the object transmittance thickness can also be restrained.

The motion period-dependent control mode and the composite mode comprising motion period-dependent control and transmittance thickness-dependent control are selected as follows. For instance, when the operator wants to obtain only a specific heartbeat time aspect with high image quality, the operator selects the motion period-dependent control mode. In the motion period-dependent control mode, when image quality deterioration is conspicuous, the operator can select the composite mode in order to control this and obtain low exposure.

Because the composite mode usually has greater advantages, the invention is also applicable to a configuration that executes only the composite mode without selection.

Figure 3:
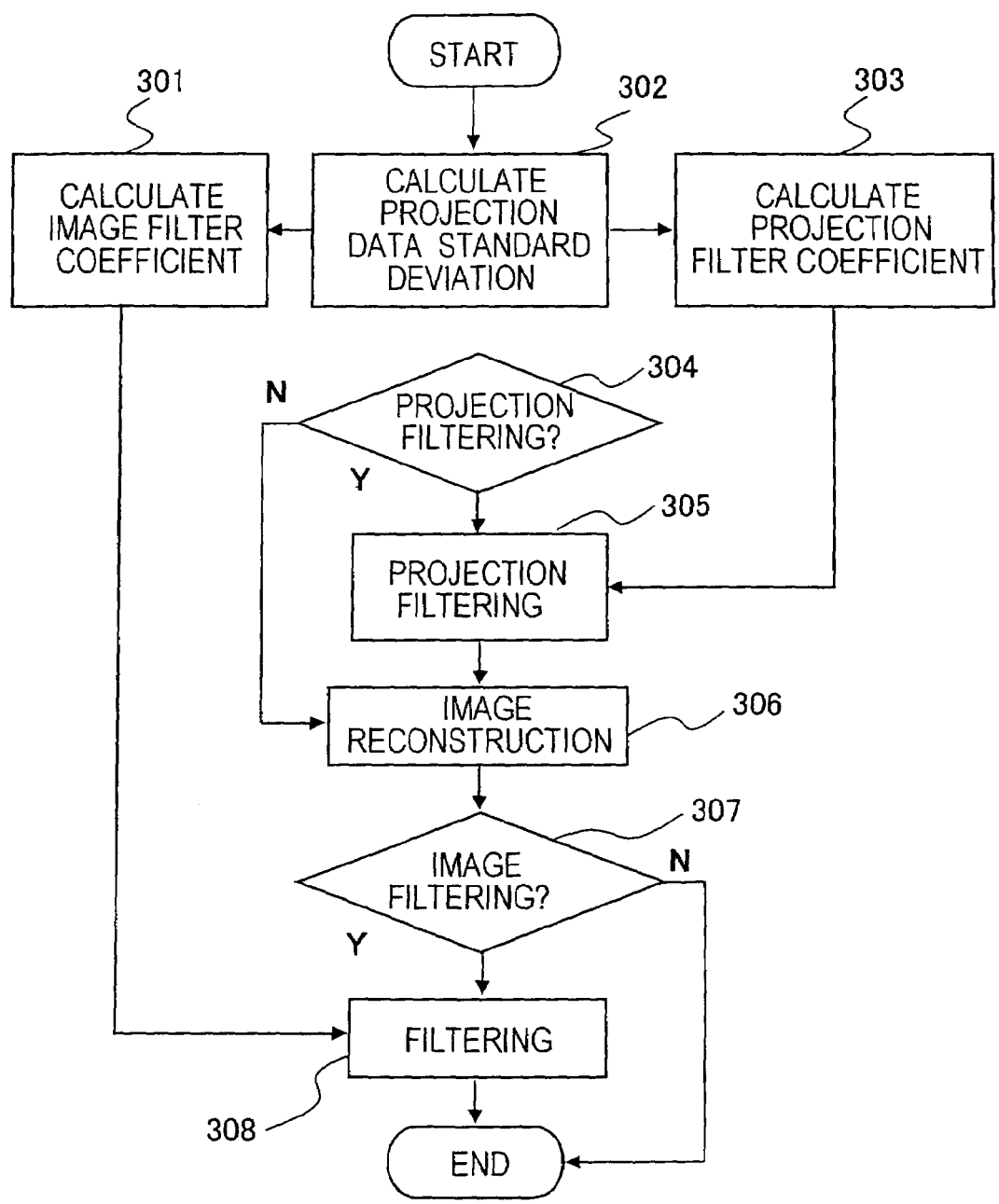
FIG. 3 is a flow chart describing an aspect of inserting filter processing.

Also, in the present embodiment, because the noise level changes per cardiac time aspect, processing steps 304 and 305 is disposed which calculates the standard deviation of the projection data, calculates the noise amount in each set of segment data, and adjusts the filter given to the projection data in response to the noise amount, as shown by 302 in the flow chart of FIG. 3. This filter processing is executed by the image processing device 106, for example. The technique may be applied by changing the reconstruction filter processing for correcting blurring of the reverse projection, or a known technique may be used such as a separate weighted average filter in the channel direction. As long as the frequency characteristics can be adjusted, the technique is not particularly limited.

According to the present embodiment, a target time aspect such as the diastolic phase is set and the tube current is raised in the target time aspect, whereby excellent image quality of the target time aspect is obtained and the evaluation of the coronary artery becomes easy. Also, because the boundary of the heart wall can be sufficiently traced even though the tube current is low in the systolic phase, the heart function can be evaluated from the volumetric ratio between the diastolic phase and the systolic phase, and all evaluations of the heart that are ordinarily necessary become possible by measuring the projection data with which a one-time tomogram can be reconstructed. In this manner, the conventional retrospective reconstruction also becomes possible.

Filter means that makes the noise level of the projection data substantially constant may also be disposed. In this case, the image quality is further stabilized. When the motion period-dependent control pattern is modulated by the transmittance thickness-dependent control pattern, the image quality of the necessary portion can be improved and the overall exposure can be reduced.

Also, when X-rays are applied only with respect to the diastolic phase, insufficiencies arise in the data due to arrhythmia, but in the imaging technique pertaining to the present invention, the insufficient data can be complemented later because the projection data are acquired at all cardiac time aspects other than the diastolic phase. In this manner, projection data of all cardiac time aspects are acquired, but data in which there is a lot of noise are also included in the projection data not intended in prospective. However, if needed, the data of an optional cardiac time aspect can be complemented even if re-exposing is not done. In this case, it becomes possible to reduce the noise with the aforementioned filter means.

Regardless of the generation or imaging mode of the X-ray CT apparatus, a technique with which the effect of improving image quality and the effect of reducing exposure are obtained is provided irrespective of 360° reconstruction or 180° reconstruction even in single-slice CT or cone-beam CT or helical scanning or dynamic scanning.

The present embodiment has been described using the heart as an example, but as mentioned previously, it will be apparent that the present invention can be applied to other periodical motion portions and imaging during voluntary periodic motion.

Embodiment 2

In a second embodiment, similar to the first embodiment, the X-ray CT apparatus configuration shown in FIG. 1 is used. Here, description will be given using the heart as the motion portion.

Figure 8:
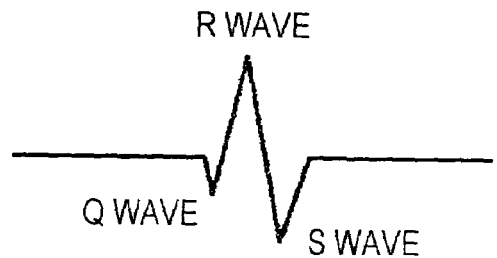
FIG. 8 is a schematic diagram of a common electrocardiograph waveform.
Figure 9:
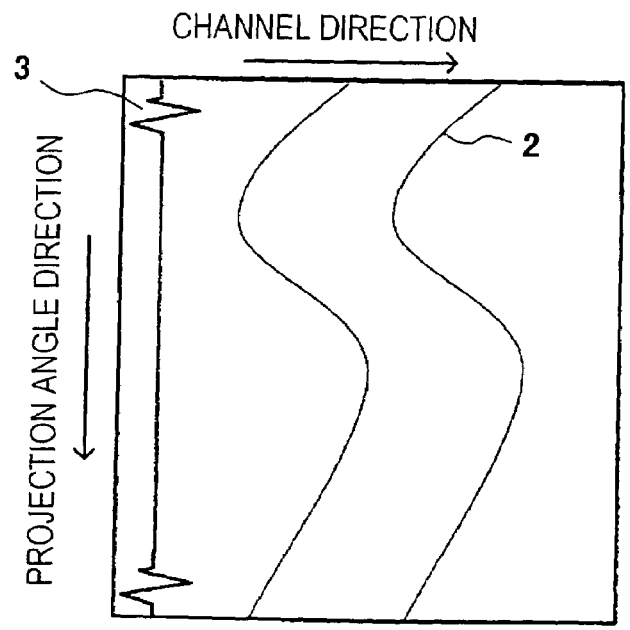
FIG. 9 is a schematic diagram of projection data.

First, portions that are the same as those in the prior art will be described. The X-ray CT apparatus ordinarily has the configuration shown in FIG. 1. The X-ray tube 101 and the detector 102 are disposed opposing each other on the scanner 100 with the object sandwiched therebetween, the heart region of the object is irradiated with X-rays from an X-ray source while using a collimator to limit the region irradiated with the X-rays, the X-rays passing through the heart region of the object are detected with the detector 102, an electrocardiograph is attached to the object as the motion information acquisition means 111, and projection data of the heart region in the vicinity of the R wave is obtained while incorporating electrocardiograph information as information of the motion portion from this electrocardiograph. FIG. 8 shows a common electrocardiograph waveform 1 in which the positions of the Q wave, the R wave and the S wave are collectively described. In the vicinity of the R wave, the heart is most dilated and the movement of the heart is at its slowest. Thus, the heart region in the vicinity of the R wave is imaged and projection data are collected while incorporating this electrocardiograph information with the electrocardiograph 111. FIG. 9 is a schematic diagram schematically showing the projection data collected in this manner. The horizontal axis in FIG. 9 represents the channel direction of the detector and the vertical axis represents the projection angle. Electrocardiograph information 3 is recorded together with projection data 2 of the heart region, but the actual projection data do not have the waveform shown in FIG. 9; rather, the position of the R wave in the projection angle is represented by a numerical value and correlated. The correlated data can be described in the data portion corresponding to detection elements at the end portions of the channel direction, for example.

Figure 10:
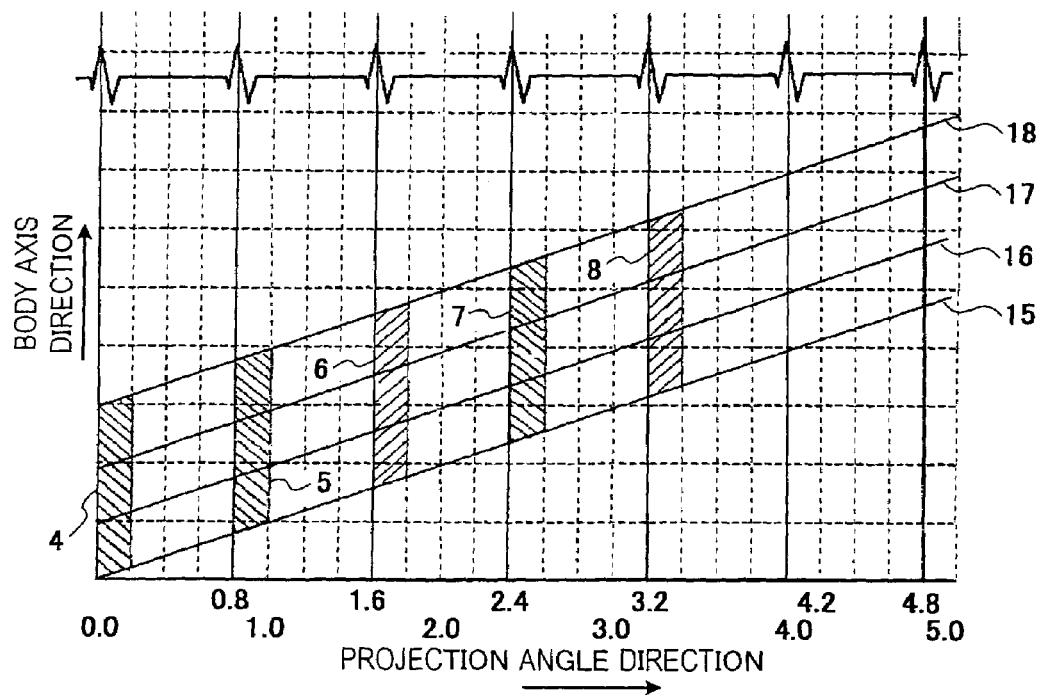
FIG. 10 is a descriptive diagram showing projection data compiling electrocardiograph information.

After the heart region is imaged, the projection data are processed in the following manner by ECG reconstruction means to obtain a reconstructed image. This will be described below as helical scanning using a 4-row multi-slice X-ray CT apparatus. As shown in FIG. 10, trajectories 15 to 18 of four detector rows are shown, and the scan periods are intervals of 1.0 seconds. As will be understood from the collectively described electrocardiograph information 3, the heartbeat periods are intervals of 0.8 seconds. After being synchronized at the 0.0 second position, the heartbeats and scanning are again synchronized after 4.0 seconds. For the projection data necessary for reconstruction, it is necessary to collect projection data whose projection angles are different and whose cardiac time aspects are the same. In FIG. 10, imaging is started from the 0.0 second position, and in the projection data until the 4.0 second (excluding the 4.0 second), the R wave occurs five times. Thus, five projection data 4 to 8 whose cardiac time aspects are different are present in 4.0 seconds. One collection region becomes projection data of 72 degrees because the projection data of 360 degrees are divided five times and collected. Converted into time, the scan period is 1.0 second, so the temporal width of one collection region is 200 ms (1 s/5 times). These projection data 4 to 8 are data whose cardiac time aspects are the same and whose projection angles are different. These projection data 4 to 8 are data whose slice positions are also different due to helical scanning. When the projection data of the collection regions 4 to 8 are shown in the range of one scan period, they appear as shown in FIG. 11.

Figure 11:
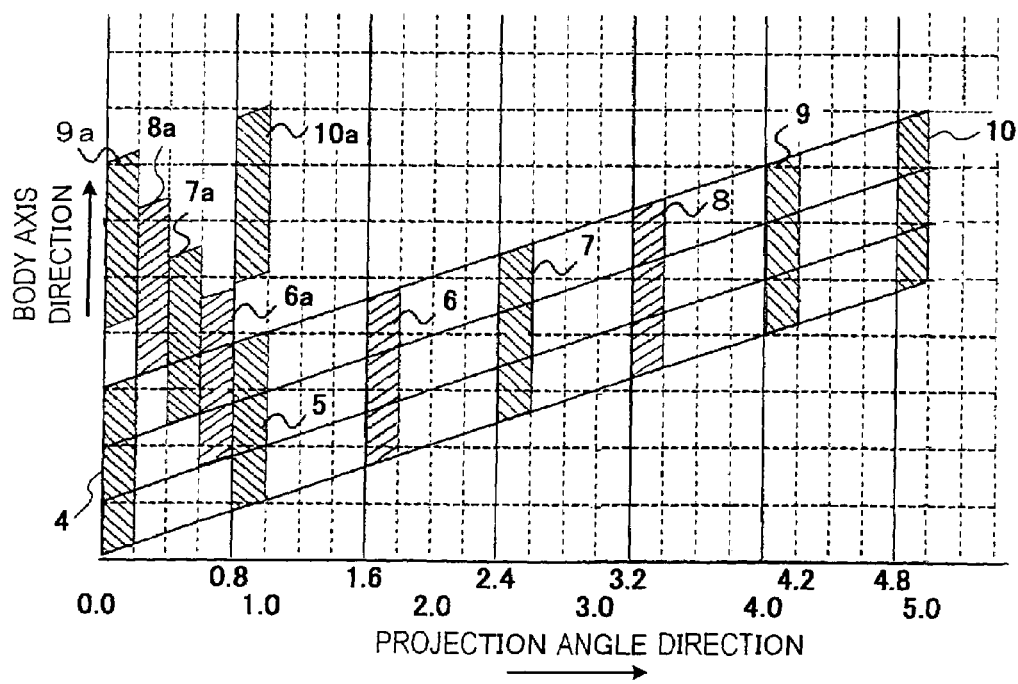
FIG. 11 is a descriptive diagram showing an initial state of a reconstruction method in a conventional X-ray CT apparatus.

The collection regions 6a to 10a in FIG. 11 are regions in which each of the collection regions 5 to 8 in FIG. 10 and collection regions 9 and 10 of 200 ms after R waves after the heartbeats and scan periods have been synchronized are transferred in parallel. The collection region 9 is projection data whose projection angle and cardiac time aspect are the same as those in the collection region 4 and whose slice position is 4 periods, i.e., 4 seconds prior. The relationship between the collection region 5 and the collection region 10 is the same as the relationship between the collection region 4 and the collection region 9. FIG. 12A shows only the relevant portion at the left side of FIG. 11. Between the collection region 4 and the collection region 9a, sometimes a discontinuous region 11 arises in the body axis direction due to helical scanning. When this discontinuous region 11 arises, simple linear interpolation or the like is used to calculate data 12 and interpolate as shown in FIG. 12B. With respect also to the discontinuous region 13 between the collection region 5 and the collection region 10a, data 14 are similarly created to interpolate. Thereafter, desired slice positions SLA and SLB are specified as shown in FIG. 12B, and reconstructed images at these specified positions are obtained.

When using a multi-slice CT apparatus that can simultaneously measure projection data of plural slice positions by plurally preparing detector rows in the body axis direction to conduct electrocardiograph synchronized reconstruction (ECG synchronized reconstruction), the time resolution can be improved by making the table speed to be low and duplicating and measuring the same slice positions. The reconstruction method used in this case is the previously mentioned method called retrospective segmented reconstruction. In other words, by measuring several times (number of segments) the region (e.g., the diastolic phase) of the cardiac time aspect of the same slice position with each detector row at the time of a helical scan, a tomogram including the time component in which the scan time necessary for creating a tomogram of that slice position is divided (time-resolved) by the number of segments can be acquired. As the time resolution is smaller, a tomogram having less influence of body movement can be obtained. For example, in the case of a 4-row multi-slice, the view range necessary for reconstruction (180°+ angle of fan in a case of half-scanning) is divided into 4 segments, and imaging conditions such as table feeding and scan time are set so that the segments can be measured by different rows. In the case of segmented reconstruction, the optimum scan time is dependent on the heart rate of the patient, but with 0.6 second scanning, an image having a time resolution of about 0.1 seconds, which is ¼ of a half scan, is acquirable.

In this method, the time resolution can be further raised because the number of segments can be increased by increasing the number of rows. For example, with 8 rows, the number of segments becomes a maximum of twice and can reach ⅛ of a half scan at the highest. In order to realize this, it is necessary to send the 4-row system and the patient table at the same speed. However, if priority is to be given to time resolution, the number of tomogram (throughput) in the body axis direction obtained during a certain scan time is not improved. As a typical example, the helical pitch is about 1.

Figure 4:
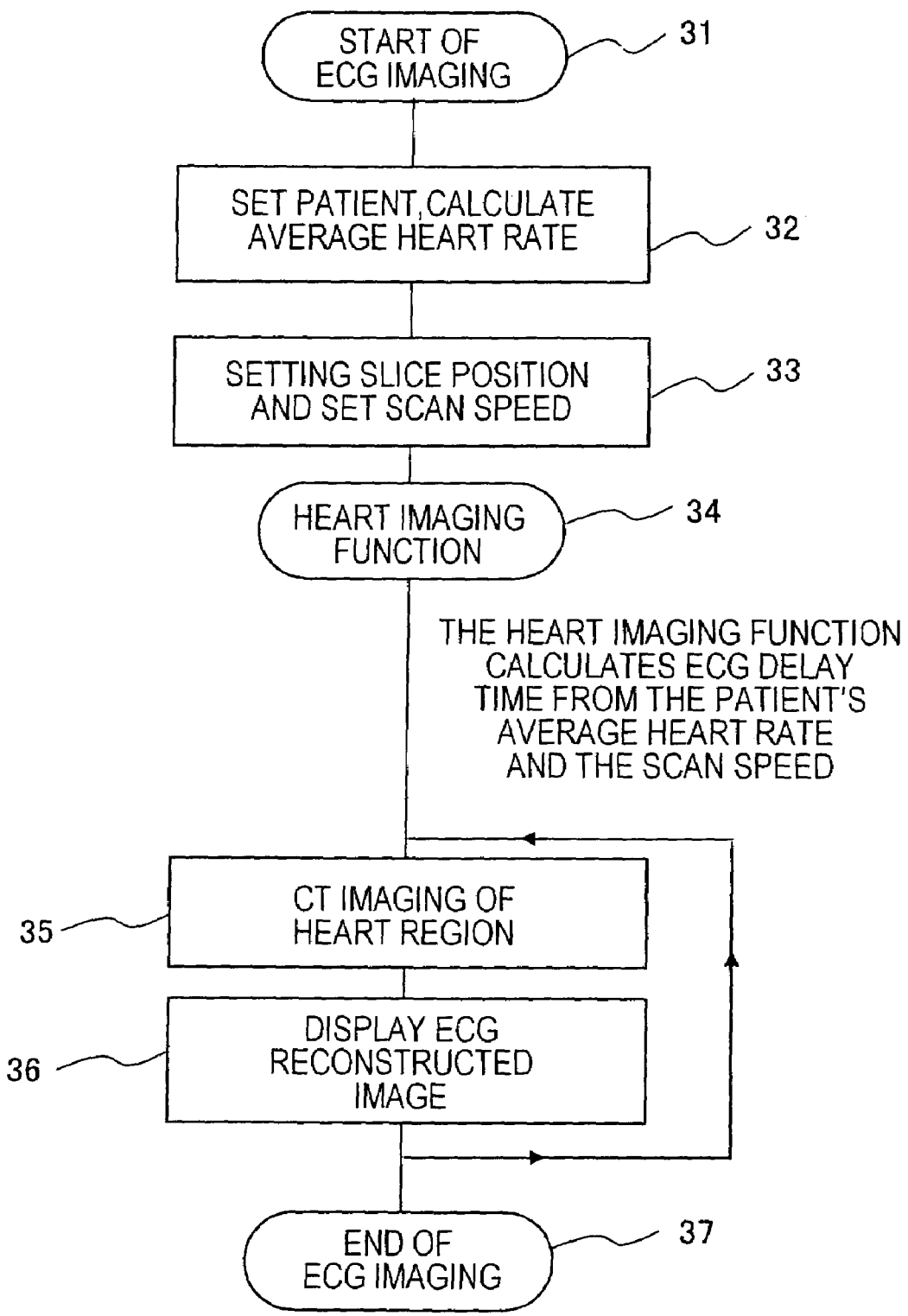
FIG. 4 is a flow chart showing the operation of the X-ray CT apparatus according to an embodiment of the present invention.

FIG. 4 is a flow chart showing the operation of the X-ray CT apparatus pertaining to the second embodiment of the invention. As will be understood from FIG. 1, the X-ray CT apparatus of the present embodiment includes: the electrocardiograph 111 that acquires electrocardiograph information of the object; the detector 102 that detects the X-rays applied to the object from the X-ray source to obtain projection data; delay time setting means that is ordinarily disposed in the host computer 107 and sets a delay time from an ECG delay time where the heartbeat phase of the electrocardiograph information is matched with the phase of the scan period and determination means that sets the slice position to be reconstructed before projection data collection; collection means such as the measurement circuit 105 that successively collects projection data of the same cardiac time aspect from the electrocardiograph information resulting from the electrocardiograph information acquisition means; and interpolation means that is ordinarily disposed in the image processing device 106 and interpolates discontinuous regions in the body axis direction of the same projection angle corresponding to the slice position after the elapse of the delay time and creates projection data; and delay time motion reconstruction means that acquires from the collection means the projection data of the slice position specified after the elapse of the delay time and reconstructs a tomogram image.

The present embodiment will be described below in accordance with the flow chart.

In step 32, after the object has been placed on the table of the X-ray CT apparatus and fixed, the electrocardiograph information of the object is acquired by the electrocardiograph information acquisition means such as an electrocardiograph to obtain the average heart rate. In step 33, prior to the collection of the projection data, the slice position of the heart region to be reconstructed is determined and the scanning speed of the X-ray CT apparatus is set. In step 34, setting characteristic of the present embodiment pertaining to the heart imaging function is conducted. In other words, the ECG delay time is calcurated from the average heart rate determined in step 32 and the scan speed set in step 33. The ECG delay time is the time until the heartbeat phase of the average heart rate and the phase of the scan period of the X-ray CT apparatus are matched, and reconstruction is started on the basis of the predetermined delay time in consideration of the system response time in the X-ray CT apparatus in addition to this ECG delay time. In step 35, CT imaging of the heart region is conducted. At this time, the electrocardiograph information obtained by the electrocardiograph 111 is referenced and the projection data of the same cardiac time aspect are successively collected by the collection means such as the measurement circuit 105. After the elapse of the predetermined delay time, discontinuous regions in the projection data in the body axis direction of the same projection angle corresponding to the initial slice position that had been set in advance are interpolated and created by the interpolation means. Using the interpolated/created data and the projection data during the elapse of the delay time in this manner, a tomogram is reconstructed by the delay time motion reconstruction means such as the image processing device 106. Because the heart is most dilated and the movement of the heart becomes the slowest in the vicinity of the R wave, a scan that is as sharp as if the heart had stopped can be obtained when reconstruction is conducted using projection data of the same portion.

In step 36, the tomogram reconstructed in this manner is displayed by the display device 109. Step 35 and step 36 are repeated in accordance with the number of slice positions, and tomograms of the slice positions are successively displayed on the display device 109.

Figure 5:
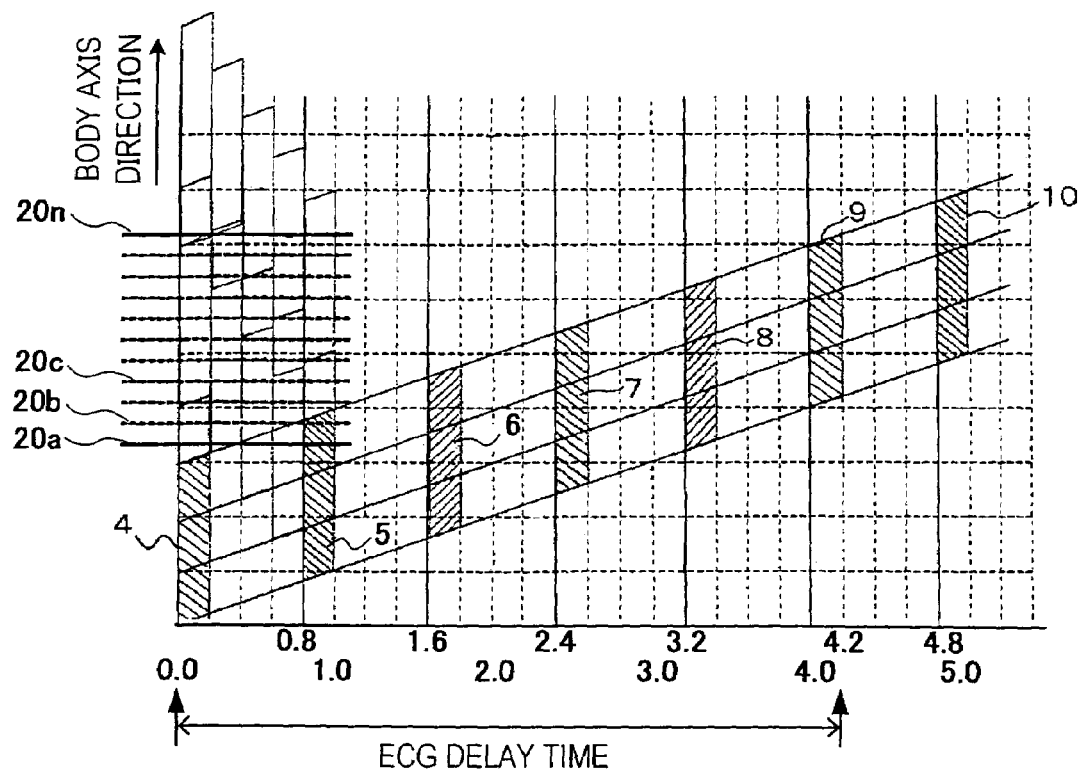
FIG. 5 is a descriptive diagram of projection data resulting from the X-ray CT apparatus shown in FIG. 4.

Next, the setting of the heart imaging of step 33 and step 34 in FIG. 4, which is the characteristic of the present embodiment, will be described in detail. In step 33, the slice position to be reconstructed is determined before the projection data collection. For example, a first slice position 20a and a final slice position 20n are determined in the body axis direction as shown in FIG. 5, setting of the number of slices between these and interval specification are conducted, and other slice positions 20b to 20m are determined as represented by the dotted lines.

Figure 7:
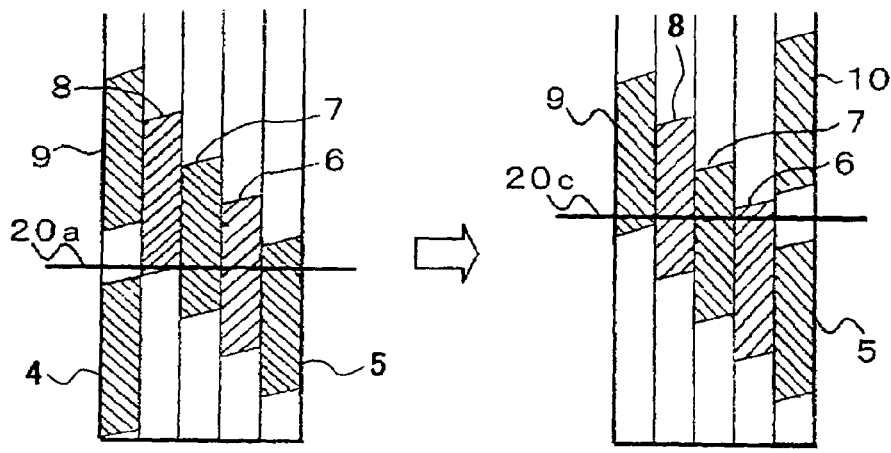
FIG. 7 is a descriptive diagram of buffering means in the X-ray CT apparatus shown in FIG. 4.

In step 34, the ECG delay time and the predetermined delay time determined from the ECG delay time are set in the delay time setting means. As already described in FIG. 7, the scan periods are 1.0 second intervals, and as will be understood from the described electrocardiograph information 3, the heartbeat periods are 0.8 second intervals. As shown in FIG. 7, the heartbeat and scan started after being synchronized at the 0.0 second position are again matched and synchronized at the 4.0 second position. The 4.2 seconds to which the temporal width of a later-described one collection region, i.e., a segment width 200 ms, has been added to the time 4.0 seconds necessary until the heartbeat phase of the electrocardiograph information 3 and the phase of the scan period are matched is the ECG delay time. On the basis of this ECG delay time 4.2 seconds, the predetermined delay time, here the response delay time of the system from the instruction of the reconstruction to the start of calculation is ideally 0 seconds, and 4.2 seconds is determined as the predetermined delay time. The function of the delay time setting means is disposed in the host computer 107, for example. The heartbeat period is obtained from the electrocardiograph 111 when calculating the predetermined delay time, but the heartbeat period can also be calculated on the basis of the R wave stored in the projection data, and the electrocardiograph information can also be separately acquired prior to the imaging of the heart region of the object.

After the predetermined delay time has been set, the heart region CT imaging of step 35 is conducted. The collection means that successively collects the projection data of the same cardiac time aspect at this time will be described. For the projection data necessary for reconstruction, it is necessary to collect projection data whose projection angles are different and whose cardiac time aspects are the same. As shown in FIGS. 5 and 12, imaging is started from the 0.0 second position, and in the projection data until the 4.0 second (excluding the 4.0 second), the R wave occurs five times. Thus, projection data whose cardiac time aspects are different are present five times as segments in 4.0 seconds. These are the collection regions 4 to 9 shown in FIG. 5. One collection region becomes projection data of 72 degrees because the projection data of 360 degrees are divided five times and collected. Converted into time, the scan period is 1.0 second, so the temporal width of one collection region is 200 ms (1 s/5 times). These projection data are data whose cardiac time aspects are the same and whose projection angles are different. The slice positions are also different due to helical scanning. The collection regions 9 and 10 represent projection data of 200 ms after the R wave after the heartbeat and the scan period have been synchronized, and are projection data whose projection angles and cardiac time aspects are the same and whose slice positions are four cycles, i.e., 4 seconds prior.

Figure 6:
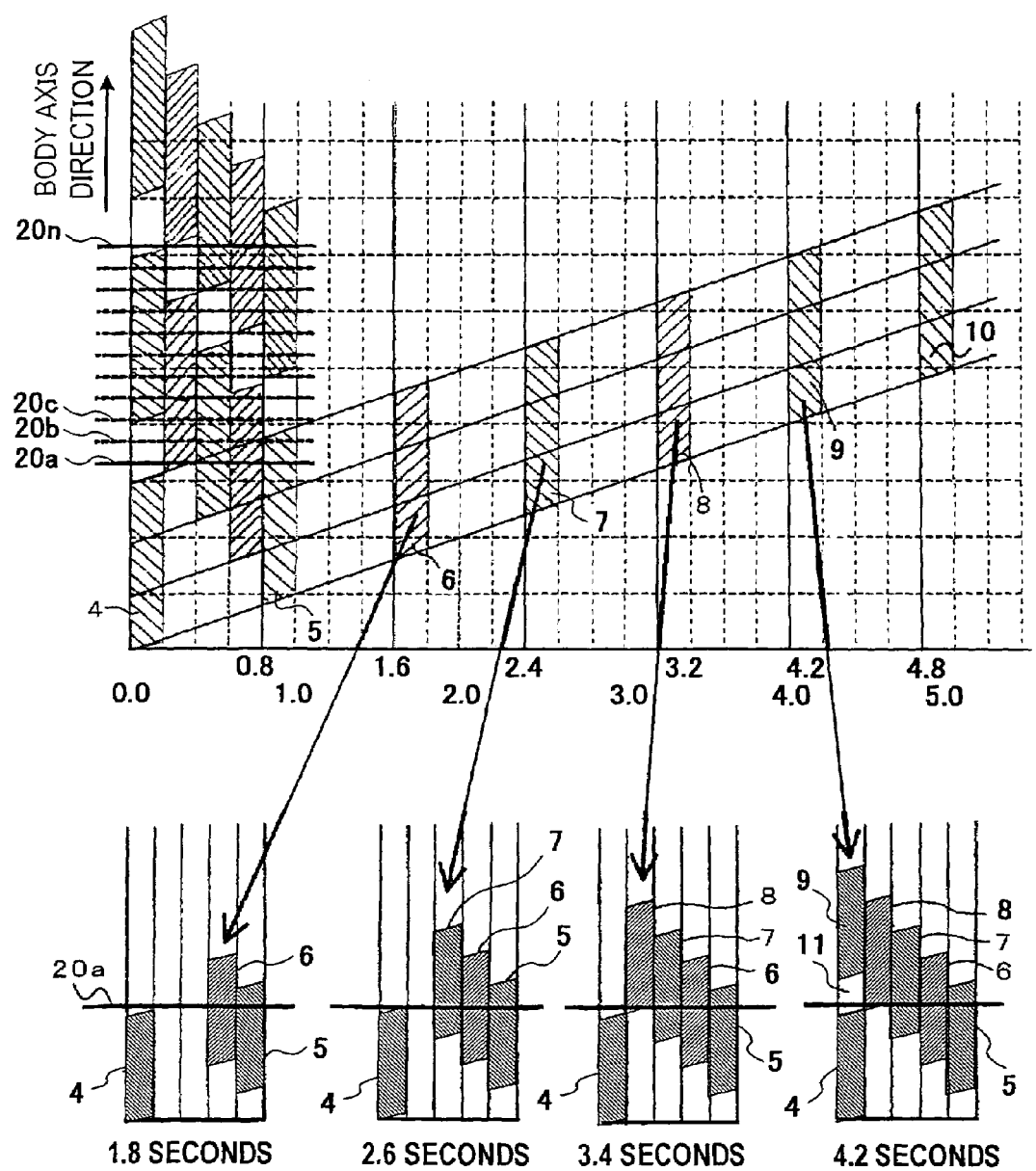
FIG. 6 are descriptive diagrams of reconstruction means in the X-ray CT apparatus shown in FIG. 4.

FIGS. 6B to 6E are descriptive diagrams showing the data collection operation by the collection means and the elapse of time. As shown in FIG. 6A, the data of the collection regions 4 to 6 are collected after 1.8 seconds after scanning is started, but at this point in time the projection data necessary for reconstruction are insufficient. Also, as shown in FIG. 6C, the data of the collection regions 4 to 7 are collected after 2.6 seconds, but at this point in time the projection data necessary for reconstruction are still insufficient. Moreover, as shown in FIG. 6D, the data of the collection regions 4 to 7 are collected after 3.4 seconds, but there are no projection data in the projection data region of the first 72 degrees. After the elapse of 4.2 seconds in FIG. 6E, the data of the collection regions 4 and 9 are matched in the same phase. However, the data 4 of the first 72 degrees does not match the slice position, and a gap region 11 arises. However, projection data can be obtained as an interpolation region by interpolation by using simple linear interpolation and calculating data from the collection region 4 and the collection region 9. At this time, the discontinuous region in the body axis direction of the same projection angle corresponding to the slice position 20a is interpolated after the elapse of the predetermined delay time by the interpolation means included in the image processing device 106, for example, to obtain projection data 11. In this manner, it eventually becomes possible to obtain a reconstructed image at the desired slice position 20a after the elapse of 4.2 seconds.

In step 36, after the elapse of the predetermined delay time, the delay time motion reconstruction means acquires from the collection means the projection data of the specified slice position 20, reconstructs a tomogram, and displays the tomogram on the display device.

According to this X-ray CT apparatus, the predetermined delay time calculated from the ECG delay time is set by the delay time setting means, and after the elapse of the predetermined delay time, the projection data of the specified slice position is acquired from the collection means, and a tomogram is reconstructed by the delay time motion reconstruction means. In regard to the method of determining the predetermined delay time from the ECG delay time, the predetermined delay time may be determined by adding a margin to the ECG delay time, for example. Here, the margin is the processing delay time such as the inter-system response time such as the time from the instruction of reconstruction processing to the start of calculation.

For this reason, it is not necessary to combine projection data and conduct image reconstruction processing after the entire heart region is imaged as has conventionally been the case. A tomogram of the slice position 20a can be reconstructed after the elapse of the predetermined delay time, and an image of the heart can be observed in real time while imaging the heart region. Moreover, projection data whose cardiac time aspects are the same and whose projection angles are different are collected by the collection means on the basis of the R wave in the electrocardiogram obtained by the electrocardiograph information collection means, and a tomogram of the slice position 20a is reconstructed by the delay time motion reconstruction means. Thus, a heart tomogram that is as sharp as if the heart had stopped can be provided after the elapse of the delay time while imaging the heart region.

The reconstruction of the next slice position 20b is conducted in the same manner following the above mentioned reconstruction of the slice position 20a. When a tomogram of the slice position 20c is to be obtained, the collection means collects the projection data of the collection regions 4 to 9 in FIGS. 6, and then at the point in time when the projection data of the next collection region 10 has been collected, i.e., when the predetermined delay time has elapsed from the collection region 5, a gap region 13 arises between the collection region 5 and the collection region 10 in the same manner as in the case of the collection region 5 and the collection region 9. However, the interpolation means is configured to interpolate the discontinuous region in the body axis direction of the same projection angle corresponding to the slice position after the elapse of the delay time and obtain projection data. Thus, when the predetermined delay time elapses from the collection region 5, linear interpolation or the like is used from the collection 5 and the collection region 10 to calculate data and obtain projection data of the gap region 13. Also, the delay time motion reconstruction means is configured to acquire from the collection means the projection data of the slice position specified after the elapse of the delay time and reconstruct a tomogram. Thus, when the predetermined delay time elapses from the collection region 5, reconstruction of the slice position 20c is conducted.

By repeating the same processing as in the case of the first slice position 20a in this manner, a tomogram that is as clear as if the heart had stopped can be obtained with respect to the slice positions 20b to 20n after the elapse of the delay time while imaging the next slice positions 20b to 20n. This processing is repeated until a tomogram of the final slice position 20n is obtained and the tomograms are successively displayed in real time on the display means. Thus, a clear image can be observed while imaging.

At this time, in order to obtain a reconstructed image of the next slice position, the X-ray CT apparatus is disposed with the collection means that successively collects projection data of the same cardiac time aspect using the electrocardiograph information resulting from the electrocardiograph, but buffering means that buffers the projection data of the same cardiac time aspect and deletes the projection data for which reconstruction has ended after the predetermined delay time may be added to the collection means. In other words, as shown in FIGS. 6B to 6E, the collection means includes buffering means that retains at least the projection data of the collection regions 4 to 8 corresponding to the predetermined delay time until the tomogram of the first slice position 20a is reconstructed by the delay time motion reconstruction means. This buffering means is the external storage means 110 of FIG. 1, for example. When the reconstruction of the tomogram of the slice position 20a is completed as shown in FIG. 7A, the buffering means deletes the projection data that is unnecessary for reconstructing the tomogram of the next slice position 20c as shown in FIG. 7B, i.e., the projection data of the collection region 4. This is successively conducted in accompaniment with the changing of the slice position to be reconstructed. The buffering means successively switches the projection data of the collection regions in this manner, whereby it can retain the projection data in order to obtain tomograms of various slice positions with a simple configuration. The buffering means may be disposed in the memory of a computer.

A case of 360 degree reconstruction has been described, but the invention can also be applied to 180 degree reconstruction. In this case, the ECG delay time is the point in time when the projection data necessary for 180 degree reconstruction have been collected, and the predetermined delay time is determined by empirically adding a little leeway to this. The delay time motion reconstruction means is disposed in the host computer 107, for example. The host computer 107 receives an instruction to start scanning from the input device 108, starts the scanning, and then clocks the predetermined delay time as described above. The host computer 107 causes the delay time motion reconstruction means 106 to conduct image reconstruction after the elapse of the predetermined delay time and displays the completed image on the display device 109. The next scan is conducted concurrently with this reconstruction.

In other words, even if reconstruction is not instructed during the imaging that continuously scans in the body axis direction and the time direction, a tomogram is obtained as soon as image-reconstructable projection data of a certain slice have been collected. Thus, the labor of the operator is reduced, it becomes possible to acquire an image in real time, and the motion artifact can be reduced. In the case where 180 degree reconstruction is used, the acquisition of the image can be more quickly conducted in comparison to 360 degree reconstruction.

In the preceding embodiments, helical scanning using a 4-row multi-slice X-ray CT apparatus was described as an example, but the present invention is not limited to this and can also be applied to imaging in a state where the table is stopped and a single slice X-ray CT apparatus.

Also, in the preceding embodiments, 4.2 seconds, which is the ECG delay time, was set as the predetermined delay time by the delay time setting means, but the predetermined delay time can be set by the delay time setting means to approach as much as possible the ECG delay time on the basis of the ECG delay time. Because the X-ray CT apparatus includes the interpolation means that includes the determination means that determines the slice position to be reconstructed prior to projection data collection and interpolates the discontinuous region in the body axis direction of the same projection angle corresponding to the slice position after the elapse of the predetermined delay time, and the delay time motion reconstruction means that acquires from the collection means the projection data of the specified slice position after the elapse of the delay time and reconstructs a tomogram, the X-ray CT apparatus can reconstruct a tomogram from a fast period after the elapse of the ECG delay time.

The invention claimed is:
1. An X-ray CT apparatus comprising:
motion information acquisition means that acquires periodical motion information on a motion portion of an object to be examined;
a detector that rotates together with an X-ray source and detects X-rays applied to the object from the X-ray source to acquire projection data per collection region;
reconstruction means that processes the projection data resulting from the detector to reconstruct a tomogram of the object; and
reconstruction time aspect specification means that specifies a time aspect in the periodical motion information to be reconstructed,
wherein the X-ray CT apparatus includes means that modulates or controls the X-ray source using a composite mode comprising a motion period-dependent control pattern and a transmittance thickness-dependent control pattern, in which control utilizing the motion period-dependent control pattern has the effect that the intensity of the X-ray applied from the X-ray becomes relatively large in the specific time aspect, and control utilizing the transmittance thickness-dependent control pattern has the effect that the intensity of the X-rays applied from the X-ray source varies depending on the X-ray transmittance thickness of the object, and an output level of the detector is maintained at a constant,
and the reconstruction means reconstructs the tomogram of the motion portion from the projection data of the collection region corresponding to the time aspect specified by the reconstruction time aspect specification means.
2. The X-ray CT apparatus of claim 1, further including
means that modulates or controls the X-ray source using motion period-dependent control pattern that controls so that the intensity of the X-rays applied from the X-ray tube becomes relatively large in the specified time aspect and
selection means that selects and executes one of the mode resulting from the motion period-dependent control pattern and the composite mode.
3. The X-ray CT apparatus of claim 1, wherein the periodical motion information is the beating of a heart.
4. The X-ray CT apparatus of claim 1, wherein the reconstruction means reconstructs using the projection data corresponding to collection regions of at least 180 degrees of the rotation.
5. The X-ray CT apparatus of claim 1, wherein the reconstruction means includes filter means that reduces the noise level difference between the collection regions or between the tomograms.
6. The X-ray CT apparatus of claim 1, wherein the minimum tube voltage is halved in the transmittance thickness-dependent control pattern.
7. The X-ray CT apparatus of claim 1, wherein control waveforms of the motion period-dependent control pattern and the transmittance thickness-dependent control patter are controlled to be sine waves.
8. The X-ray CT apparatus of claim 1, wherein the motion period-dependent control pattern is selected when operator wants to obtain only a specific heartbeat time aspect with high image quality, and the composite mode is selected when image quality is conspicuous in the motion period-dependent control pattern.

9. An X-ray CT apparatus comprising:
- a detector configured to rotate together with an X-ray source and detect X-rays applied to an object to be examined from the X-ray source to acquire projection data per collection region:
- motion information acquisition means configured to acquire periodical motion information on a motion portion of the object to be examined;
- reconstruction time aspect specification means configured to specify a time aspect in the periodical motion information to be reconstructed;
- an image processing part configured to process the projection data from the detector to reconstruct a tomogram of the object, the image processing part reconstructing the tomogram of the motion portion from the projection data of the collection region corresponding to the time aspect specified by the reconstruction time aspect specification means; and
- an X-ray control part configured to modulate and control the X-ray source in a composite mode comprising a motion period-dependent control pattern and a transmittance thickness-dependent control pattern, wherein
- control utilizing the motion period-dependent control pattern causes the intensity of the X-ray from the X-ray source to become relatively large in the specific time aspect, and
- control utilizing the transmittance thickness-dependent control pattern causes the intensity of the X-rays from the X-ray source to vary depending on an X-ray transmittance thickness of the object.

10. The X-ray CT apparatus of claim 9, wherein the motion portion of the object includes one or more of a heart, a lung, a diaphragm, an artery, an intestine and a ventriculus of the object.

11. The X-ray CT apparatus of claim 9, wherein the image processing part reconstructs using the projection data corresponding to collection regions of at least 180 degrees of the rotation.

12. The X-ray CT apparatus of claim 9, wherein the image processing part includes a filter that reduces a noise level difference between the collection regions or between the tomograms.

13. The X-ray CT apparatus of claim 9, wherein the minimum tube voltage is halved in the transmittance thickness-dependent control pattern.

14. The X-ray CT apparatus of claim 9, wherein control waveforms of the motion period-dependent control pattern and the transmittance thickness-dependent control pattern are controlled to be sine waves.

15. The X-ray CT apparatus of claim 9, wherein only the motion period-dependent control pattern is selected when obtaining a specific heartbeat time aspect with high image quality is desired, and the composite mode is selected when image quality is conspicuous in the motion period-dependent control pattern.

16. An X-ray CT method comprising:
- rotating a detector together with an X-ray source, and detecting X-rays applied to an object to be examined from the X-ray source to acquire projection data per collection region;
- acquiring periodical motion information on a motion portion of the object to be examined;
- specifying a time aspect in the periodical motion information to be reconstructed;
- processing the projection data from the detector to reconstruct a tomogram of the object, and reconstructing the tomogram of the motion portion from the projection data of the collection region corresponding to the specified time aspect; and
- modulating and controlling the X-ray source in a composite mode comprising a motion period-dependent control pattern and a transmittance thickness-dependent control pattern, wherein control utilizing the motion period-dependent control pattern causes the intensity of the X-ray from the X-ray source to become relatively large in the specific time aspect, and control utilizing the transmittance thickness-dependent control pattern causes the intensity of the X-rays from the X-ray source to vary depending on an X-ray transmittance thickness of the object.

17. The X-ray CT method of claim 16, further comprising controlling waveforms of the motion period-dependent control pattern and the transmittance thickness dependent control pattern to be sine waves.

18. The X-ray CT method of claim 16, further comprising selecting only the motion period-dependent control pattern when obtaining a specific heartbeat time aspect with high image quality is desired.

19. The X-ray CT method of claim 16, further comprising selecting the composite mode when image quality is conspicuous in the motion period-dependent control pattern.

* * * * *